(12) United States Patent
Krieglstein et al.

(10) Patent No.: US 6,933,127 B2
(45) Date of Patent: Aug. 23, 2005

(54) SUBSTRATE FOR PP2C

(75) Inventors: Josef Krieglstein, Cölbe (DE);
Susanne Klumpp, Marburg (DE)

(73) Assignee: EUCRO European Contract Research GmbH & Co. KG, Neuss (DE)

( * ) Notice: Subject to any disclaimer, the term of this patent is extended or adjusted under 35 U.S.C. 154(b) by 56 days.

(21) Appl. No.: 10/188,374

(22) Filed: Jul. 3, 2002

(65) Prior Publication Data

US 2003/0044875 A1 Mar. 6, 2003

(30) Foreign Application Priority Data

Jul. 5, 2001 (EP) .............................................. 01250251

(51) Int. Cl.$^7$ .............................. C12Q 1/42; C12N 9/16; G01N 33/53; A61K 38/17; A61K 31/66
(52) U.S. Cl. .......................... 435/21; 435/196; 435/7.1; 514/12; 514/75; 530/352
(58) Field of Search ........................... 435/21, 196, 7.1; 514/17

(56) References Cited

FOREIGN PATENT DOCUMENTS

| EP | 0 566 535 A1 | 10/1993 |
|---|---|---|
| WO | WO 99/02167 | 1/1999 |
| WO | WO 99/27134 | 6/1999 |
| WO | WO 00/35946 | 6/2000 |
| WO | WO 01/10888 A1 | 2/2001 |
| WO | WO 02/02629 A2 | 1/2002 |
| WO | WO 02/13798 A2 | 2/2002 |
| WO | WO 02/064737 A2 | 8/2002 |

OTHER PUBLICATIONS

Klumpp et al., "Purification and characterization of protein phosphatase type 2C in photoreceptors," Methods in Enzymology 315:570–578–, 2000.*

Wang et al., "Ca2+-induced apoptosis through calcineurin dephosphorylation of BAD," Science 284:339–343, 1999.*

Abstract of EP 0 566 535 A1—English.

XP–001098159—Review Article—Serine/threonine protein phosphatases, Stefaan WERA et al., Biochem J. (1995) 311, 17–29 (Printed in Great Britain) pp. 39–51.

XP008022476—Syndromes of Accelerated Atherosclerosis: Role of Vascular Injury And Smooth Muscle Cell Proliferation, John H. IP et al., JACC vol. 15, No. 7, 1990 by the American College of Cardiology, pp. 1667–1687.

XP–002211494—Protein phosphatase 2A activates the proapoptotic function of BAD in interleukin–3–dependent lymphoid cells by a mechanism requiring 14–3–3 dissociation, Chi–Wu Chiang et al., BLOOD, Mar. 1, 2001—vol. 97, No. 5, pp. 1289–1297.

U.S. Appl. No. 10/189,188.

* cited by examiner

*Primary Examiner*—Robert A. Wax
*Assistant Examiner*—Rosanne Kosson
(74) *Attorney, Agent, or Firm*—Millen, White, Zelano & Branigan, P.C.

(57) ABSTRACT

The invention relates to a combination of a protein phosphatase type 2C as an enzyme and a phospho-BAD as substrate. The protein BAD is dephosphorylated in position Ser$^{155}$. Furthermore, the combination is used in an in vitro screening for ligands which modulate protein phosphatase type 2C, comprising the steps: incubating the protein phosphatase type 2C in combination with the substrate phospho-BAD and the ligand of the assay and detecting the decrease in phospho-BAD and/or the increase in phosphate and/or BAD. Therefore, new drugs for the treatment apoptosis may be found.

8 Claims, No Drawings

SUBSTRATE FOR PP2C

The invention relates to a substrate for protein phosphatase type 2C (=PP2C) which substrate is dephosphorylated by PP2C. The invention further relates to a screening for ligands modulating the activity of protein phosphatase type 2C.

State of the Art Protein Phosphatase Type 2C

Protein phosphatase type 2C (PP2C) is one of the four major serine/threonine protein phosphatases (PP1, PP2A, PP2B=calcineurin, PP2C) found in eukaryotic cells and classified according to biochemical criteria (Ingebritsen, T. S. and Cohen, P. (1983) Protein phosphatases: Properties and role in cellular regulation. *Science* Vol: 221, 331–337 and Wera, S. and Hemmings, B. A. (1995) Serine/threonine protein phosphatases. *Biochem. J.* Vol: 311, 17–29). The dephosphorylation activity of PP2C absolutely requires the presence of $Mn^{2+}$ or $Mg^{2+}$ ions (McGowan, C. H. and Cohen, P. (1988) Protein phosphatase-2C from rabbit skeletal muscle and liver: A $Mg^{2+}$-dependent enzyme. *Meth. Enzymol.* Vol 159, 416–426). PP2C activity is not sensitive to the tumor promotor okadaic acid or other inhibitors known to affect many of the serine/threonine phosphatases (Cohen, P., Holmes C. F. B. and Tsukitani, Y. (1990) Okadaic acid: a new probe for the study of cellular regulation. *TIBS* Vol: 15, 98–102). Dephosphorylation of [$^{32}$P]casein in the presence of 20 mM $Mg^{2+}$ is considered the standard technique to determine PP2C activity in vitro (McGowan, C. H. and Cohen, P. (1988) Protein phosphatase-2C from rabbit skeletal muscle and liver: A $Mg^{2+}$-dependent enzyme. *Meth. Enzymol.* Vol 159, 416–426).

Serine/threonine protein phosphatases are subdivided phylogenetic into the PPP family (comprising PP1, PP2A, PP2B) and the PPM family ($Mg^{2+}$-dependent) (Cohen, P. T. W (1994) Nomenclature and chromosomal localization of human protein serine/threonine phosphatase genes. *Adv. Prot Phosphatases* Vol 8, 371–276). PPP stands for phospho-protein-phosphatase and PPM stands for protein phosphatase Mg-dependent. PP2C relates to the main enzyme subtype of PPM. Molecular cloning has defined PP2Cs as distinct protein phosphatases, since they constitute a separate gene family and are monomeric enzymes. The predominant isotypes in mammalian cells are PP2Cα (PPM1A) and PP2Cβ (PPM1B), which are separate gene products of 43–48 kDa (identity 77%) (Cohen, P. T. W (1994) Nomenclature and chromosomal localization of human protein serine/threonine phosphatase genes. *Adv. Prot. Phosphatases* Vol: 8, 371–276 and Mann, D. J., Campbell, D. G., McGowan, C. H. and Cohen, P. T. W. (1992) Mammalian protein serine/threonine phosphatase type 2C: cDNA cloning and comparative analysis of amino acid sequences. *Biochem. Biophys. Acta* Vol: 1130, 100–104). The mammalian PP2C family in addition includes PP2Cγ (also called FIN13), PP2Cδ and WIP1 (Guthridge, M. A., Bellosta, P., Tavoloni, N. and Basilico, C. (1997) FIN13, a novel growth factor-inducible serine-threonine phosphatase which can inhibit cell cycle progression. *Mol. Cell. Biol.* Vol: 17, 5485–5498 and Tong, Y., Quirion, R. and Shen S. -H. (1998) Cloning and characterization of a novel mammalian PP2C isozyme. *J. Biol. Chem.* Vol: 273, 35282–35290 and Fiscella, M., Zhang, H. L., Fan, S., Sakaguchi, K., Shen, S., Mercer, W. E., vande Woude, G. F., O'Connor P. M., and Appella, E. (1997) Wip1, a novel human protein phosphatase that is induced in response to ionizing radiation in a p53-dependent manner. *Proc. Natl. Acad. Sci. USA* Vol: 94, 6048–6053).

The list of potential physiological functions proposed for PP2Cα and PP2Cβ comprises a wide range. A growing list of substrates has been described to be specifically dephosphorylated by PP2Cα and PP2Cβ, indicating an involvement in various metabolic pathways.

(i) Hydroxymethylglutaryl-CoA reductase (Ball, K. L., Dale, S., Weekes J. and Hardie, D. G. (1994) Biochemical characterization of tow forms of 3-hydroxy-3-methylglutaryl-CoA reductase kinase from cauliflower (*Brassica oleracia*). *Eur. J. Biochem.* Vol: 219, 743–750);

(ii) AMP-activated protein kinase (Davies, S. P., Helps, N. R., Cohen, P. T. W. and Hardie, D. G. (1995) 5'-AMP inhibits dephosphorylation, as well as promoting phosphorylation, of the AMP-activated protein kinase. Studies using bacterially expressed human protein phosphatase-2Cα and native bone protein phosphatase-1$A_C$. *FEBS Lett.* Vol: 377, 421–425);

(iii) $Ca^{2+}$-calmodulin-dependent protein kinase II (Fukunaga, K., Kobayashi, T., Tamura, S. and Miyamoto, E. (1993) Dephosphorylation of autophosphorylated $Ca^{2+}$/Calmodulin-dependent protein kinase II by protein phosphatase 2C. *J. Biol. Chem.* Vol: 268, 133–137);

(iv) P38 mitogen-activated protein kinase (MAPK) plus MAPK4 and MAPK6 (Terasawa, T., Kobayashi, T., Murakami, T., Ohnishi, M., Shunsuke, K., Tanaka, O., Kondo, H., Yamamoto, H., Takeuchi, T. and Tamura, S. (1993) Molecular cloning of a novel isotype of $Mg^{2+}$-dependent protein phosphatase β (Type 2Cβ) enriched in brain and heart. *Arch. Biochem. Biophys.* Vol: 307, 342–349.13);

(v) Cystic fibrosis transmembrane conductance regulator (Travis, S. M., Berger, H. A. and Welsh, M. J. (1997) Protein phosphatase type 2C dephosphorylates and inactivates cystic fibrosis transmembrane conductance regulator. *Proc. Natl. Acad. Sci.* Vol: 94,1105511060); and (vi) Cyclic-dependent kinases CDK2 and CDK6 (Cheng, A., Kaldis P. and Solomon M. J. (2000) Dephosphorylation of human cyclin-dependent kinases by protein phosphatase type 2Cα and β2 isoforms. *J. Biol. Chem.* Vol: 275, 34744–34749).

Pro-Apoptotic Oncogene BAD

BAD (BAD stands for Bcl-2/Bcl-$X_L$-antagonist, causing cell death) represents a point of convergence of several different signal-transduction pathways which are activated by survival factors inhibiting apoptosis in mammalian cells. BAD is a pro-apoptotic protein which binds to the anti-apoptotic proteins Bcl-2 and Bcl-$X_L$ (Yang, E., Zha, J., Jockel, J. Bioise, L. H., Thompson, C. B. and Korsemeyer, S. J. (1995) Bad, a heterodimeric partner for Bcl-$X_L$ and Bcl-2 displaces Bax and promotes cell death. *Cell* Vol: 80, 285–291). This interaction is thought to neutralize the anti-apoptotic effects of Bcl-2/Bcl-$X_L$ and may represent one of the mechanisms by which BAD promotes apoptosis. Phosphorylation of BAD results in its interaction with 14-3-3 proteins instead of Bcl-2 or Bcl-$X_L$, leading to liberation of these anti-apoptotic proteins which can then interact with Bax to inhibit apoptosis (Zha, J., Harada, H., Yang, E., Jokel, J. and Korsemeyer, S. J. (1996) Serine phosphorylation of death agonist BAD in response to survival factor results in binding to 14-3-3 not Bcl-$X_L$. *Cell* Vol: 87, 618–628). Two sites on BAD, $Ser^{112}$ and $Ser^{136}$ have been reported to be phosphorylated in vivo. The dephosphorylation of those sites was shown to be carried out by PP1 and PP2B (Ayllon, V., Martinez-A., C., Garcia, A., Cayla, X. and Rebollo, A. (2000) Protein phosphatase 1α is a ras-activated bad phosphatase that regulates interleukin-2 deprivation-induced apoptosis. *EMBO J.* Vol: 19, 2237–2246 and Wang, H. G., Pathan, N., Ethell, I. M., Krajewski, S., Yamaguchi, Y., Shibasaki. F., McKeon, F., Bobo, T., Franke, T. F. and Reed, J. C. (1999) $Ca^{2+}$-induced apoptosis through calcineurin dephosphorylation of BAD. *Science* Vol: 284, 339–343). In addition, PP2A also has also been reported to act on phospho-BAD (Deng, X., Ito, T., Carr, B., Mumby, M. and May, W. S. (1998) Reversible phosphorylation of Bcl2 following interleukin 3 or bryostatin 1 is mediated by direct interaction with protein phosphatase 2A. *J. Biol. Chem.* Vol: 273, 34157–34163). The major site on BAD phosphorylated by PKA in vitro just recently discovered was $Ser^{155}$. The phosphorylation of $Ser^{155}$ triggers the dissociation of BAD from Bcl-2 and Bcl-$X_L$ and promotes its interaction with 14-3-3 proteins (Lizcano, J. M., Morrice, N. and Cohen, P. (2000) Regulation of Bad by cAMP-dependent protein kinase is mediated via phosphorylation of a novel site, $Ser^{155}$. *Biochem. J.* Vol: 349, 547–557).

Moreover, all the information on dephosphorylation of BAD so far is focussed on the phosphorylation sites $Ser^{112}$ and $Ser^{136}$—there is no information on $Ser^{155}$, one of the two sites crucial for the interaction with Bcl-$X_L$ (Lizcano et al. 2000). There are no studies on whether phospho-BAD could be a substrate for PP2C, because an inhibitor specifically affecting PP2C has not been available. BAD occupies a pivotal position in regulating the start and maintenance of apoptosis. No modulator for phospho-BAD has been found in order to offer a drug for therapy of apoptosis.

Problem and Solution

It is the problem of the invention to provide a substrate for PP2C which substrate represent relevant physiological conditions concerning to specific therapies. The intention is to find modulators which can be used in the treatment of apoptosis, especially neuronal apoptosis.

The problem is solved by a combination comprising
(i) a protein phosphatase type 2C as an enzyme and
(ii) a phospho-BAD as substrate.

It is self-evident that the combination is only used in vitro. Further compounds such as $Mg^{2+}$ may be necessary to increase enzymatic activity to a sensible, physiological value.

In addition, the problem is solved by an in vitro use of a protein phosphatase type 2C as an enzyme for converting the substrate phospho-BAD to the product BAD and inorganic phosphate.

Further the problem is solved by an in vitro use of phospho-BAD as a substrate for the protein phosphatase type 2C.

Preference is given to the combination according to the invention, wherein the protein phosphatases type 2C are selected from the group PP2Cα; PP2Cβ; PP2Cγ; and PP2Cδ. More preference is given to the combination according to the invention, wherein the protein phosphatases type 2C are selected from the group PP2Cα and PP2Cβ. Most preference is given to the combination of the invention wherein the protein phosphatase type 2C is the PP2Cβ. The proteins PP2Cα; PP2Cβ; PP2Cγ; and PP2Cδ comprise subtypes, for example PP2Cβ1; PP2Cβ2; PP2Cβ3; PP2Cβ4; and PP2Cβ5 (Arch. Biochem. Biophys. 307, 342–349 (1993), Terasawa et al., molecular cloning of a novel isotype of $Mg^{2+}$-dependent protein phosphatase β enriched in brain and heart; Biochem. and Mol. Biol. Int. 32, 773–780 (1994), Hou et al., molecular cloning of cDNAs encoding two isoforms of protein phosphatase 2Cβ from mouse testis; Arch. Biochem. 318, 387–393 (1995), Kato et al., molecular cloning and expression of mouse Mg-dependent protein phosphatase type 2Cβ-4).

Preference is given to the combination according to the invention wherein the protein BAD is obligatorily phosphorylated in position $Ser^{155}$, and facultatively phosphorylated in positions $Ser^{112}$ and/or $Ser^{136}$. Most preferred is a combination according to the invention, wherein the protein phospho-BAD is phosphorylated in position $Ser^{155}$.

A further solution of the problem is the use of the combination of the invention in an in vitro screening for ligands which modulate the protein phosphatase type 2C, comprising the steps:

(i) incubating protein phosphatase type 2C in combination with the substrate phospho-BAD and the ligand of the assay and (ii) detecting the decrease in phospho-BAD and/or the increase in phosphate and/or BAD.

Preference is given to the use of the combination according to the invention in an in vitro screening, wherein the aforementioned screening is executed and furthermore, a control is added comprising the steps of the above mentioned screening of (i) incubating and (ii) detecting, wherein the addition of the ligand of the assay is omitted.

The invention also comprises control assays which are not done simultaneously with the ligand assays. It is possible, to execute the control only once and to compare the actual measured value representing the presence of the ligand with the control value measured before.

The addition of more than one ligand is possible in order to reduce the number of reaction wells.

in vivo: In vivo techniques stands for methods for treatment of human or animal body by surgery or therapy and diagnostic methods practiced on the human or animal body.

in vitro: The expression in vitro exclude all in vivo techniques and methods mentioned above. Further the expression in vitro in this application refers to cultures, such as cell cultures, tissue cultures, parts of organs, organs, systems of organs and parts of animal body, especially human body. All these specimen are removed from the animal organism. The specimen will not be re-introduced into the animal (including human) organism. Preference is given to the expression in vitro which stands for scientific and/or commercial experiments characterized by an artificial system using cells, fractions thereof, purified components or homogenates, outside of a living organism.

Ligands: The expression ligand comprises all types of naturally occurring or synthetically produced chemical substances, capable of binding protein phosphatase type 2C and modulating the enzymatic activity of the chemical conversion of phospho-BAD to BAD and phosphate. In this text the ligand is the assay substance or the ligand of the assay.

Detection: The decrease in phospho-BAD or the increase in BAD and/or phosphate is measured according to the examples and according to the standard literature:

(aa) autoradiographic labeling using for example [$^{32}$P] BAD;

(bb) antibodies against phospho-BAD $Ser^{112}$, phospho BAD $Ser^{136}$, phospho BAD $Ser^{155}$, and also against BAD. The last group of antibodies against BAD recognizes domains which are not influenced by the state of BAD phosphorylation.

Further processes of identification are possible.

Modulation: Modulation stands for decrease or increase in the enzymatic activity of protein phosphatase type 2C in respect to the conversion of phospho-BAD to phosphate and BAD, especially phospho-BAD in position Ser[155]. The value of the decreased or increased enzymatic activity is measured comparing the value of the enzymatic activity of an identical assay system but omitting the ligand in assay.

Preferred is an in vitro screening for a ligand according to the invention, wherein the test systems are cell-free systems or enzymatic test systems.

Cell-free system: To obtain a cell-free system, the cell membranes or cell walls are destroyed, and cell membrane fragments and cell wall fragments are partially or completely removed for example by centrifugation, from the interior of the cells (cytosol). In the cytosol the activity of enzymes and the metabolite can be measured. In some assay cases the cell-free system may comprise membrane fragments containing PP2C.

Enzymatic assay: In enzymatic assays specific enzymes and if necessary cofactors are used to catalyze specific substrates. The changes in substrate concentrations educts and/or product concentrations are measured. The enzymatic assay may comprise a cascade of special enzymes and substrates which are described in the state of the art.

Advantages

It is a great advantage to regulate BAD phosphorylation by useing protein phosphatase PP2C. Regulation of BAD depends on the catalytic activity of PP2C, which should be modulated by compounds. Therefore, the invention teaches how to find modulators of PP2C under physiological conditions, which are relevant for the development and maintaninace of apoptosis. Inhibitors of PP2C will be useful drugs in the therapy of stroke, apoptosis, and other degenerative diseases.

All other PP2C substrates mentioned in the state of the art are important for the metabolism of fat or for other pathways. The in vitro screening based on the invention makes it possible to select natural or synthetic compounds. In the state of the art there is no known inhibitor of PP2C is known, because no physiologically relevant assay system for finding ligands is available. In particular, the ligands found by the inventive screening can be used for supporting or prevention or curing brain tissue after stroke and other neurodegenerative diseases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

1. Materials and Methods 1.1. Dephosphorylation of Phospho-BAD

Dephosphorylation of phospho-BAD by PP2C is assayed in vitro using recombinant BAD (Lizcano, J. M., Morrice, N. and Cohen, P. (2000) Regulation of Bad by cAMP-dependent protein kinase is mediated via phosphorylation of a novel site, Ser[155]. Biochem. J. Vol: 349, 547–557) kindly provided by Sir Philip Cohen, Dundee, UK. cDNA encoding PP2Cβ from bovine brain was expressed in E. Coli and purified using Ni-NTA-Sepharose. (J. Neurosci. Res. 51, 328–338 (1998) Protein phosphatase type-2C isozymes present in vertebrate retinae: purification, characterization, and localization in photoreceptors.)

1.2. Phosphorylation of BAD:

Incubations were carried out for 30 min at 37° C. The reaction mixture (12 μl) contained 12 μg BAD (GST-fusion protein) (Lizcano et al. (2000) Biochem. J. 349, 547–557), 0.55 μg PKA (Sigma), 1 μM ATP, 15 μCi [γ-$^{32}$P]ATP, 5 mM MgCl$_2$ and 25 mM Tris/HCl pH 7.5. After incubation at 37° C. for 30 min, hot and cold ATP were removed by centrisep centrifugation columns. This was necessary to avoid continuous phosphorylation upon the second incubation when phosphatase activities were assayed.

1.3. Dephosphorylation of Phospho-BAD:

The substrate used ([$^{32}$P]BAD) was prepared as described above. After the centrisep step, [$^{32}$P]BAD was diluted 10-fold using 25 mM Tris/HCl pH 7.5. Incubations (15 μl) were carried out for 30 min at 37° C. (unless mentioned otherwise) with 9 μl [$^{32}$P]BAD (0.2 μg), 1.5 μl 10-fold reactionbuffer (200 mM Tris/HCl pH 7.5, 100 mM MgCl$_2$, 10% glycerol, 1% 2-mercaptoethanol), and 0.3 μg of PP2C. The reactions were stopped by the addition of 5 μl of denaturing sample buffer and kept on ice until proteins were separated on 12.5% SDS-PAGE minigels. (De-) Phosphorylation was visualized by autoradiography.

2. Results from the Assay Systems

Dephosphorylation of BAD by PP2C is time- and protein-dependent, and requires the presence of Mg$^{2+}$-ions, which is characteristic for PP2C.

TABLE I

Dephosphorylation of phospho - BAD by PP2Cβ
Time - dependence

| Reaction time in min | PP2Cβ | Value of [$^{32}$P]BAD |
| --- | --- | --- |
| 0 | + | +++++ |
| 5 | + | ++++ |
| 10 | + | +++ |
| 20 | + | ++ |
| 30 | + | + |
| 30 | − (control) | +++++ |

Dephosphorylation of [$^{32}$P]BAD depends on the time of incubating PP2Cβ together with the substrate phospho-BAD which is cleaved to give phosphate and BAD. The concentration of [$^{32}$P]BAD is measured in this assay, therefore intensive spots on the X-ray sensitive film represent high concentrations of [$^{32}$P]BAD, in other words low activity of the enzyme PP2Cβ.

TABLE II

Dephosphorylation of phospho - BAD by PP2Cβ
Protein - dependence

| [PP2Cβ] in ng | Reaction time in min | Value of [$^{32}$P]BAD |
| --- | --- | --- |
| 0 | 30 | ++++++ |
| 15 | 30 | +++++ |
| 30 | 30 | ++++ |
| 60 | 30 | +++ |
| 150 | 30 | ++ |
| 300 | 30 | + |
| 300 | 0 (control) | ++++++ |

The concentration of the enzyme PP2Cβ correlates with the concentration of the products BAD and phosphate. In this specific case the intensive spots represent low concentrations of the products BAD and phosphate.

TABLE I

Dephosphorylation of phospho - BAD by PP2Cβ
$Mg^{2+}$ - dependence

| Addition of | Presence of PP2Cβ | Reaction time in min | Value of [$^{32}$P]BAD |
|---|---|---|---|
| 5 mmol/l EGTA | − | 30 | ++++ |
| 0.1 mmol/l $Mg^{2+}$ | − | 30 | ++++ |
| 1 mmol/l $Mg^{2+}$ | − | 30 | ++++ |
| 10 mmol/l $Mg^{2+}$ | − | 30 | +++ |
| 5 mmol/l EGTA | + | 30 | +++ |
| 0.1 mmol/l $Mg^{2+}$ | + | 30 | +++ |
| 1 mmol/l $Mg^{2+}$ | + | 30 | ++ |
| 10 mmol/l $Mg^{2+}$ | + | 30 | + |
| — | + | 0 (control) | ++++ |

The activity of the enzyme depends on the concentration of $Mg^{2+}$ ions. More $Mg^{2+}$ ions increases the enzymatic activity.

The entire disclosure of all applications, patents and publications, cited herein and of corresponding European application No. 01250251.4, filed Jul. 5, 2001 is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for in vitro screening for a ligand which modulates protein phosphatase type 2C activity, comprising:

(i) incubating the protein phosphatase type 2C in combination with phospho-BAD and a sample comprising the ligand;

(ii) measuring the amount of phospho-BAD, inorganic phosphate or BAD; and (iii) comparing to the amount of phospho-BAD, inorganic phosphate, or BAD produced in a control reaction in which the sample does not comprise in the ligand;

wherein an increase or decrease in phospho-BAD, inorganic phosphate, or BAD in the presence of the ligand compared to the absence of the ligand indicates that the ligand is a modulator of protein phosphatase type 2C activity.

2. A method of claim 1, wherein a decrease in phospho-BAD, increase in inorganic phosphate, or increase in BAD compared to the control indicates that the phosphatase activity is increased in the presence of the ligand.

3. A method of claim 1, wherein an increase in phospho-BAD, decrease in inorganic phosphate, or decrease in BAD compared to the control indicates that the phosphatase activity is inhibited in the presence of the ligand.

4. A method according to claim 1, wherein the protein phosphatase type 2C is PP2Cα; PP2Cβ; PP2Cγ; or PP2Cδ.

5. A method according to claim 4, wherein the protein phosphatase type 2C is PP2Cα or PP2Cβ.

6. A method according to claim 5, wherein the protein phosphatase type 2C is PP2Cβ.

7. A method according to claim 1, wherein the protein BAD is obligatorily phosphorylated in position $Ser^{155}$, and facultatively phosphorylated in position $Ser^{112}$ and/or $Ser^{136}$.

8. A method according to claim 1, wherein the protein BAD is phosphorylated in position $Ser^{155}$.

* * * * *

UNITED STATES PATENT AND TRADEMARK OFFICE
CERTIFICATE OF CORRECTION

PATENT NO. : 6,933,127 B2
DATED : August 23, 2005
INVENTOR(S) : Josef Krieglstein et al.

It is certified that error appears in the above-identified patent and that said Letters Patent is hereby corrected as shown below:

<u>Column 8,</u>
Line 9, reads "comprise in the ligand" should read -- comprise the ligand --.

Signed and Sealed this

Fourth Day of April, 2006

JON W. DUDAS
*Director of the United States Patent and Trademark Office*